US007445786B1

(12) United States Patent
Rehtanz et al.

(10) Patent No.: US 7,445,786 B1
(45) Date of Patent: Nov. 4, 2008

(54) DIAGNOSING AND PROTECTING AGAINST TURSIOPS TRUNCATUS PAPILLOMAVIRUS

(76) Inventors: Manuela Rehtanz, 345 E. 24th St., 921 D, New York, NY (US) 10010; A. Bennett Jenson, 1517 E. Washington St., Louisville, KY (US) 40206; Shin-je Ghim, 223B S. Hancock St., Louisville, KY (US) 40202; Gregory D. Bossart, 5600 U.S. 1 North, Fort Pierce, FL (US) 34946

( * ) Notice: Subject to any disclaimer, the term of this patent is extended or adjusted under 35 U.S.C. 154(b) by 0 days.

(21) Appl. No.: 11/733,557

(22) Filed: Apr. 10, 2007

Related U.S. Application Data

(60) Provisional application No. 60/744,554, filed on Apr. 10, 2006.

(51) Int. Cl.
*A61K 39/12* (2006.01)
(52) U.S. Cl. .................................. 424/204.1; 435/6
(58) Field of Classification Search ............. 424/204.1; 435/6
See application file for complete search history.

(56) References Cited

U.S. PATENT DOCUMENTS

| | | | |
|---|---|---|---|
| 5,057,411 | A | 10/1991 | Lancaster et al. |
| 5,283,171 | A | 2/1994 | Manos et al. |
| 5,639,606 | A | 6/1997 | Willey |
| 5,643,765 | A | 7/1997 | Willey |
| 5,874,089 | A | 2/1999 | Schlegel et al. |
| 6,153,201 | A | 11/2000 | Rose et al. |
| 6,165,471 | A | 12/2000 | Garcea et al. |
| 6,485,728 | B2 | 11/2002 | Schlegel et al. |
| 6,887,478 | B2 | 5/2005 | Schlegel et al. |
| 6,908,615 | B1 | 6/2005 | Hofmann et al. |
| 7,001,995 | B1 | 2/2006 | Neeper et al. |
| 2002/0197264 | A1 | 12/2002 | Schlegel et al. |
| 2004/0086527 | A1 | 5/2004 | Schlegel et al. |
| 2005/0026257 | A1 | 2/2005 | Gissmann et al. |
| 2005/0282263 | A1 | 12/2005 | McCormick et al. |
| 2006/0029612 | A1 | 2/2006 | Palmer et al. |

OTHER PUBLICATIONS

Rehtanz et al., "Isolation and characterization of the first American bottlenose dolphin papillomavirus: *Tursiops truncatus* papillomavirus type 2", Journal of General Virology, 87, 2006, pp. 3559-3565.
Bossart et al., "Cutaneous papovaviral-like papillomatosis in a killer whale (*Orcinus orca*)", Mar. Mamm. Sci., 12, 2006, pp. 274-281.
Bossart et al., "Viral papillomatosis in Florida manatees (*Trichechus manatus latirostris*)", Exp. Mol. Pathol., 72, 2002, pp. 37-48.
Bossart et al., "Orogenital neoplasia in Atlantic bottlenose dolphins (*Tursiops truncates*)", Aquatic Mammals, 31(4), 2005, pp. 473-480.
Ghim et al., "Equine papillomavirus type 1: complete nucleotide sequence and characterization of recombinant virus-like particles composed of the EcPV-1 L1 major capsid protein", Bioch. Biophys. Res. Commun., 324(3), 2004, pp. 1108-1115.
Jenson et al. "Multiplicity of Uses of Monoclonal Antibodies That Define Papillomavirus Linear Immunodominant Epitopes", Immunol. Res., 16, 1997, pp. 115-119.
Lambertsen et al., "Genital papillomatosis in sperm whale bulls", J.Zoo Wildl. Med., 23, 1997, pp. 374-379.
Pastrana et al., "Cross-neutralization of cutaneous and mucosal Papillomavirus types with anti-sera to the amino terminus of L2", Virology, 337, 2005, pp. 365-372.
Rector et al., "Characterization of a Novel Close-to-Root Papillomavirus from a Florida Manatee by Using Multiply Primed Rolling-Circle Amplification: *Trichechus manatus latirostris* Papillomavirus Type 1", J. Virol., 78, 2004, pp. 12698-12702.
Van Bressem et al., "Genital and lingual warts in small cetaceans from coastal Peru", Dis. Aquat. Org., 26, 1996, pp. 1-10.
Van Bressem, M. F., "Natural history of virus infections in cetaceans", PhD thesis, University off Liège, 1997.
Van Bressem et al., Cutaneous papillomavirus infection in harbour porpoise (*Phocoena phocoena*) from the North Sea, Vet. Rec., 144, 1999a, pp. 592-593.
Van Bressem et al., "A review of virus infections of cetaceans and the potential impact of morbilliviruses, poxviruses and papillomaviruses on host population dynamics", Dis. Aquat. Org., 38, 1999b, pp. 53-65.
Jenson et al., "Immunologic relatedness of papillomaviruses from different species", Journal of the National Cancer Institute, 64, 1980, pp. 495-500.
Yuan, et al., "An epidermotropic canine papillomavirus with malignant potential contains an E5 gene and establishes a unique genus", Virology, 359, 2007; pp. 28-36.
Ghim et al., "Cervical cancer, etiology, pathogenesis treatment and future vaccines", Asian Pacific Journal of Cancer Prevention, 3, 2002, pp. 207-214.
Nakai et al., "Monoclonal Antibodies to Genus- and Type-Specific Papillomavirus Structural Antigens", Intervirology, 25, 1986, pp. 30-37.

*Primary Examiner*—Ali R. Salimi
(74) *Attorney, Agent, or Firm*—Stites & Harbison PLLC; Mandy Wilson Decker

(57) ABSTRACT

Composition for conferring protection against *Tursiops truncatus* papillomavirus (TtPV) infection in a subject includes a virus-like particle assembled from at least one type of TtPV L1 protein. Methods for protecting a subject against TtPV infection include administering to the subject an immunogenic composition including a virus-like particle assembled from at least one type of TtPV L1 protein. Methods for diagnosing TtPV infection in a subject include providing a virus-like particle assembled from at least one TtPV L1 protein; contacting the virus-like particle with serum obtained from the subject; and identifying the subject as having TtPV infection if a TtPV antibody capable of binding the virus-like particle is detected in the serum.

11 Claims, 7 Drawing Sheets

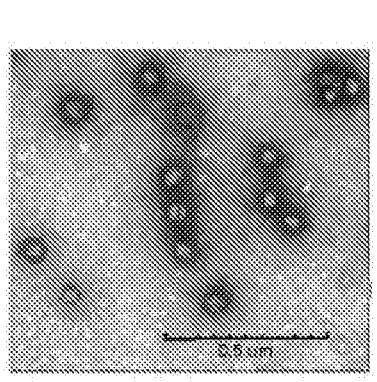 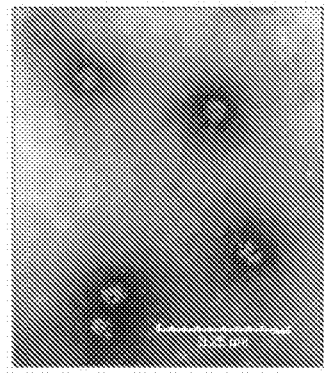 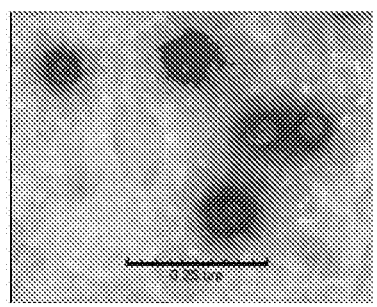
FIGURE 8A	FIGURE 8B	FIGURE 8C
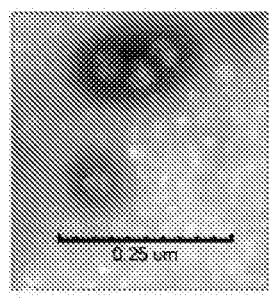 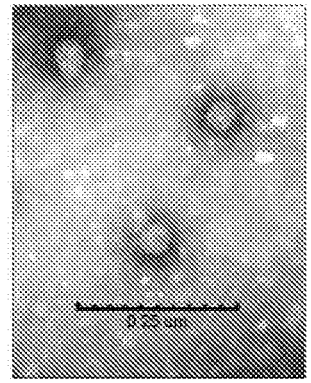
FIGURE 9A	FIGURE 9B
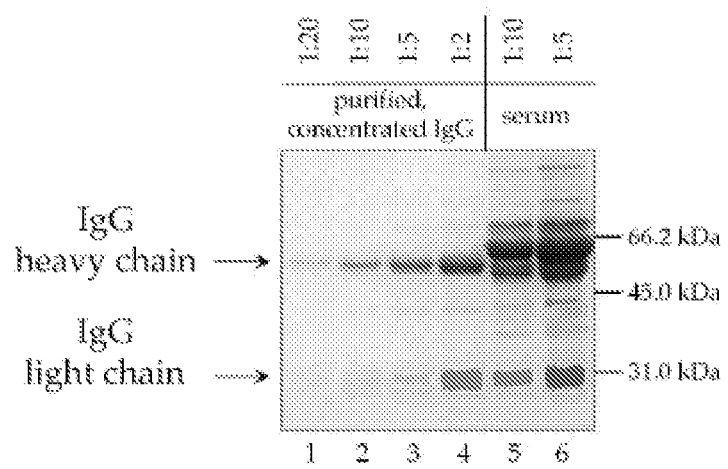
FIG. 10

|   |  | rabbit 1: immunized with TtPV-1 VLPs | | | | rabbit 2: immunized with TtPV-1 VLPs | | | |
|---|---|---|---|---|---|---|---|---|---|
|   |   | E | F | | | G | H | | |
|   | 1st Ab \ VLPs | Pre-serum | Serum | | | Pre-serum | Serum | | |
|   |   | 1:100 | 1:100 | 1:500 | 1:1,000 | 1:100 | 1:100 | 1:500 | 1:1,000 |
| A | TtPV-1 0.1 µg int. particles | 0.003 | 0.653 | 0.638 | 0.633 | 0.004 | 0.388 | 0.193 | 0.120 |
| B | 4.0 µg den. particles | 0.008 | 0.032 | 0.025 | 0.022 | 0.007 | 0.038 | 0.024 | 0.025 |
| C | TtPV-2 0.1 µg int. particles | 0.003 | 0.173 | 0.056 | 0.038 | 0.002 | 0.244 | 0.100 | 0.056 |
| D | 4.0 µg den. particles | 0.005 | 0.023 | 0.021 | 0.021 | 0.006 | 0.025 | 0.019 | 0.021 |

FIG. 11

SEQUENCE LISTING

<160> NUMBER OF SEQ ID NOS: 4

<210> SEQ ID NO 1
<211> LENGTH: 1539
<212> TYPE: DNA
<213> ORGANISM: Tursiops truncatus

<400> SEQUENCE: 1

```
atgctgcagc tgcctcctcc aggcgccctt aaccgggtgt tgcacaccga tgaatttatt      60
gttcgcacca atgcatttta ccatgctatg acagaacgcc ttattaccat aggcaaccca     120
tattatcggg tgaagggga atctgaaggg tctgtgatag ctgaaaaggt gtcacctcat     180
cagtacaggg tgtttcgcat tcagctgcct gatcccaatc agcttgcttt ggtagacgcc     240
agtgtgtatg accccaagtc tgaaagacta gtgtggctgc tcaggggctt tgatattggc     300
agaggcggcc ctttgggtgt tggtgccacc ggccatcctt tgtttgataa gctaaaggat     360
gcagaaaacc ctaataatgc atatactaat ttggagaaaa ctgattccag gcaaaatgtg     420
tgtatggatc ccaaatctat gcaaatgatt attgttgggt gcacccctgc tgttggccac     480
tattgggaca aggctgatgc atgtccttcc attgctcctc caaagcctgg agcgtgtcct     540
gccttagtgc ttaaaaacag tcccttggag gatggtgaca tgattgattt agggttcggt     600
agcatgaata acaaagccct taatgaaagc cactctgctg ttcccttaga cattgtaaac     660
tctattacta agcaccctga tatgcttaaa atggctgctg agccttatgg aaactcatgc     720
tggttctgcc ttgtcaggga gcaaatgttt gctcgtcatt tgtgggctag aaatggtgaa     780
attggtgatg ctgttcccaa tgcttttgaa catgctgctg atagcttgta tttaaccagt     840
agcagcaatg gtgaacgggc ccacatggct actcctgcgt atttgtgcac cccaagtggt     900
tctctggttt ctagcgacac ccaggtgttt aatcggccat tttggttgca acgagcacaa     960
ggcagaaaca atggcgcctg ctggcacaat gaactctttg tgtctattgc agacaataca    1020
cgtggtacta actttaacat ttctgttaag gctgatggta aggctattga tgggcttat    1080 aagtataagg gggatgattt taagcagtac gtgcgacact gtgagatatt tgagctaacc    1140
tttattatcc agctcggtaa agtgtctctt actgcagagg cggttgctca tctacaaggc    1200
atggacgctt ccattttaga ggagtggaac atcgggtttc agggcaccgc cactgtatct    1260
gctgaggaaa aatataggta tttgtcctct cttgccacta aatgccctga taaccctccc    1320
actcctaagg tgcaagatag atatgatggg ttgtccttt ggactgtgga tgtgtctaaa    1380
acattgtcta aggatttaga aaattacccc ttaggtagaa aatttctata ccaggctggc    1440
ctaaccaatg gtgttcctgc cactaggaaa cgcacctcag gtggtccctc ctctaagctc    1500
cccactaagc gcaaacgcag gaaggtgaca cgtacctaa                            1539
```

<210> SEQ ID NO 2
<211> LENGTH: 512
<212> TYPE: PRT
<213> ORGANISM: Tursiops truncatus

<400> SEQUENCE: 2

Met Leu Gln Leu Pro Pro Pro Gly Ala Leu Asn Arg Val Leu His Thr

-continued

```
1               5                   10                  15

Asp Glu Phe Ile Val Arg Thr Asn Ala Phe Tyr His Ala Met Thr Glu
                20                  25                  30

Arg Leu Ile Thr Ile Gly Asn Pro Tyr Tyr Arg Val Lys Gly Glu Ser
                35                  40                  45

Glu Gly Ser Val Ile Ala Glu Lys Val Ser Pro His Gln Tyr Arg Val
                50                  55                  60

Phe Arg Ile Gln Leu Pro Asp Pro Asn Gln Leu Ala Leu Val Asp Ala
65                              70                  75                  80

Ser Val Tyr Asp Pro Lys Ser Glu Arg Leu Val Trp Leu Leu Arg Gly
                85                  90                  95

Phe Asp Ile Gly Arg Gly Gly Pro Leu Gly Val Gly Ala Thr Gly His
                100                 105                 110

Pro Leu Phe Asp Lys Leu Lys Asp Ala Glu Asn Pro Asn Asn Ala Tyr
                115                 120                 125

Thr Asn Leu Glu Lys Thr Asp Ser Arg Gln Asn Val Cys Met Asp Pro
                130                 135                 140

Lys Ser Met Gln Met Ile Ile Val Gly Cys Thr Pro Ala Val Gly His
145                             150                 155                 160

Tyr Trp Asp Lys Ala Asp Ala Cys Pro Ser Ile Ala Pro Pro Lys Pro
                165                 170                 175

Gly Ala Cys Pro Ala Leu Val Leu Lys Asn Ser Pro Leu Glu Asp Gly
                180                 185                 190

Asp Met Ile Asp Leu Gly Phe Gly Ser Met Asn Asn Lys Ala Leu Asn
                195                 200                 205

Glu Ser His Ser Ala Val Pro Leu Asp Ile Val Asn Ser Ile Thr Lys
                210                 215                 220

His Pro Asp Met Leu Lys Met Ala Ala Glu Pro Tyr Gly Asn Ser Cys
225                             230                 235                 240

Trp Phe Cys Leu Val Arg Glu Gln Met Phe Ala Arg His Leu Trp Ala
                245                 250                 255

Arg Asn Gly Glu Ile Gly Asp Ala Val Pro Asn Ala Phe Glu His Ala
                260                 265                 270

Ala Asp Ser Leu Tyr Leu Thr Ser Ser Asn Gly Glu Arg Ala His
                275                 280                 285

Met Ala Thr Pro Ala Tyr Leu Cys Thr Pro Ser Gly Ser Leu Val Ser
                290                 295                 300

Ser Asp Thr Gln Val Phe Asn Arg Pro Phe Trp Leu Gln Arg Ala Gln
305                             310                 315                 320

Gly Arg Asn Asn Gly Ala Cys Trp His Asn Glu Leu Phe Val Ser Ile
                325                 330                 335

Ala Asp Asn Thr Arg Gly Thr Asn Phe Asn Ile Ser Val Lys Ala Asp
                340                 345                 350

Gly Lys Ala Ile Asp Gly Ala Tyr Lys Tyr Lys Gly Asp Asp Phe Lys
                355                 360                 365

Gln Tyr Val Arg His Cys Glu Ile Phe Glu Leu Thr Phe Ile Ile Gln
                370                 375                 380

Leu Gly Lys Val Ser Leu Thr Ala Glu Ala Val Ala His Leu Gln Gly
385                             390                 395                 400

Met Asp Ala Ser Ile Leu Glu Glu Trp Asn Ile Gly Phe Gln Gly Thr
                405                 410                 415

Ala Thr Val Ser Ala Glu Glu Lys Tyr Arg Tyr Leu Ser Ser Leu Ala
                420                 425                 430
```

Thr Lys Cys Pro Asp Asn Pro Pro Thr Pro Lys Val Gln Asp Arg Tyr
        435                 440                 445

Asp Gly Leu Ser Phe Trp Thr Val Asp Val Ser Lys Thr Leu Ser Lys
        450                 455                 460

Asp Leu Glu Asn Tyr Pro Leu Gly Arg Lys Phe Leu Tyr Gln Ala Gly
465                 470                 475                 480

Leu Thr Asn Gly Val Pro Ala Thr Arg Lys Arg Thr Ser Gly Gly Pro
                485                 490                 495

Ser Ser Lys Leu Pro Thr Lys Arg Lys Arg Arg Lys Val Thr Arg Thr
            500                 505                 510

<210> SEQ ID NO 3
<211> LENGTH: 1524
<212> TYPE: DNA
<213> ORGANISM: Tursiops truncatus

<400> SEQUENCE: 3

```
atgctgcata taccacctcc aggacccttta gacagggttt tgcatactga tgaatttgtg      60
caacgcacta atgcatttta ttatgcatct acagagcgcc aaataattat aggaaatccc     120
tactttaagg ttgtaggtga caatcacag gtgatcgcag agaaggtgtc cccacatcaa      180
tttaggtttt ttaggctgtt gctgcctgat ccaaataagt ttgccttaat agactctaat    240
gtgtatgatg ctaaaacaga acggttggtg tggctccttc ggggggtttga tgtaggacgt    300
ggtggtgccc ttggtgttgg tgccactgga catccactgt ttgacaagtt aagagatgca    360
gaaaatccaa acaataacta caacaaaaca gaacaaaaag atgctaggca aaatgtgtgc    420
atagatccaa atcaatgca atgatactt gtaggttgca cctgctgt tggacagcat        480
tgggatattg ctagcacctg caaagatgcc caaccacctc ctggcagttg ccctccattg    540
gaattaagga atactactat tgaggatggg gacatgatgg atttaggatt tggcagtatg    600
aacaacaaag cattaaatgc atcacattct gcagttcctt tagacatagt tgactccatt    660
accaagcacc ctgacatgct taaaatggcg gcggaccgtt atggtaatgc ttgctggttt    720
tgtgttgtac gtgaacaaat gtttgccagg catttgtggg ctagaaatgg tgtaacgggt    780
gataatatac cacatgcttt gcaacatgag cctgatagcc tgtacttaac cagtgattca    840
gaggatagac aaaccttgtc ctcttcagca tacatgtgta cacccagtgg ttctatggtg    900
tccagtgata ctcaactctt caataggcct ttttggttgc aacgtgcaca aggcaaaaac    960
aatgggtctc gctggaataa tgagttgttt gtgtccattg ttgataatac tagaggcaca   1020
aacctgtcaa tttctgtgaa acgtgatggg gaaccattag gtaagcagtc taaatataaa   1080
gcagaagatt ttaagcagta tgtaagcaca ctgtgagatat ttgatgtgtc ccttgtattg   1140
cagttgggga gagtgccttt aacagctgaa gcagtagcac accttaatgc aatggatcct   1200
gatatattgc gtgggtggaa cataggcttt caagcagctg cccctgtatc tggagaagaa   1260
aattacagat atttgtcctc cctggctact aaatgccctg atattccacc tgcagaggtg   1320
ccaaaatcta ggtatgatgg aatgtcattt tggactatag atgtgtctaa atctctcaca   1380
gcggatcttg acaattatac actaggaaga aagttccttt accaggctgg attatccacc   1440
cgtgggtcta ctactggacg taagcgtcgt gcctccccag ccatttcacg gtctaagggg   1500
aaacgcaggc gtactaaaca gtaa                                           1524
```

<210> SEQ ID NO 4
<211> LENGTH: 507

```
<212> TYPE: PRT
<213> ORGANISM: Tursiops truncatus

<400> SEQUENCE: 4
```

| | | | | | | | | | | | | | | |
|---|---|---|---|---|---|---|---|---|---|---|---|---|---|---|
| Met | Leu | His | Ile | Pro | Pro | Gly | Pro | Leu | Asp | Arg | Val | Leu | His | Thr |
| 1 | | | | 5 | | | | | 10 | | | | | 15 |
| Asp | Glu | Phe | Val | Gln | Arg | Thr | Asn | Ala | Phe | Tyr | Tyr | Ala | Ser | Thr | Glu |
| | | | 20 | | | | | 25 | | | | | 30 |
| Arg | Gln | Ile | Ile | Ile | Gly | Asn | Pro | Tyr | Phe | Lys | Val | Gly | Glu | Gln |
| | | 35 | | | | | 40 | | | | | 45 |
| Ser | Gln | Val | Ile | Ala | Glu | Lys | Val | Ser | Pro | His | Gln | Phe | Arg | Val | Phe |
| 50 | | | | | 55 | | | | | 60 |
| Arg | Leu | Leu | Leu | Pro | Asp | Pro | Asn | Lys | Phe | Ala | Leu | Ile | Asp | Ser | Asn |
| 65 | | | | | 70 | | | | | 75 | | | | | 80 |
| Val | Tyr | Asp | Ala | Lys | Thr | Glu | Arg | Leu | Val | Trp | Leu | Arg | Gly | Phe |
| | | | 85 | | | | | 90 | | | | | 95 |
| Asp | Val | Gly | Arg | Gly | Gly | Ala | Leu | Gly | Val | Gly | Ala | Thr | Gly | His | Pro |
| | | | 100 | | | | | 105 | | | | | 110 |
| Leu | Phe | Asp | Lys | Leu | Arg | Asp | Ala | Glu | Asn | Pro | Asn | Asn | Tyr | Asn |
| | | 115 | | | | | 120 | | | | | 125 |
| Lys | Thr | Glu | Gln | Lys | Asp | Ala | Arg | Gln | Asn | Val | Cys | Ile | Asp | Pro | Lys |
| 130 | | | | | 135 | | | | | 140 |
| Ser | Met | Gln | Met | Ile | Leu | Val | Gly | Cys | Thr | Pro | Ala | Val | Gly | Gln | His |
| 145 | | | | | 150 | | | | | 155 | | | | | 160 |
| Trp | Asp | Ile | Ala | Ser | Thr | Cys | Lys | Asp | Ala | Gln | Pro | Pro | Gly | Ser |
| | | | 165 | | | | | 170 | | | | | 175 |
| Cys | Pro | Pro | Leu | Glu | Leu | Arg | Asn | Thr | Thr | Ile | Glu | Asp | Gly | Asp | Met |
| | | | 180 | | | | | 185 | | | | | 190 |
| Met | Asp | Leu | Gly | Phe | Gly | Ser | Met | Asn | Asn | Lys | Ala | Leu | Asn | Ala | Ser |
| | | | 195 | | | | | 200 | | | | | 205 |
| His | Ser | Ala | Val | Pro | Leu | Asp | Ile | Val | Asp | Ser | Ile | Thr | Lys | His | Pro |
| 210 | | | | | 215 | | | | | 220 |
| Asp | Met | Leu | Lys | Met | Ala | Ala | Asp | Arg | Tyr | Gly | Asn | Ala | Cys | Trp | Phe |
| 225 | | | | | 230 | | | | | 235 | | | | | 240 |
| Cys | Val | Val | Arg | Glu | Gln | Met | Phe | Ala | Arg | His | Leu | Trp | Ala | Arg | Asn |
| | | | 245 | | | | | 250 | | | | | 255 |
| Gly | Val | Thr | Gly | Asp | Asn | Ile | Pro | His | Ala | Leu | Gln | His | Glu | Pro | Asp |
| | | | 260 | | | | | 265 | | | | | 270 |
| Ser | Leu | Tyr | Leu | Thr | Ser | Asp | Ser | Glu | Asp | Arg | Gln | Thr | Leu | Ser | Ser |
| | | | 275 | | | | | 280 | | | | | 285 |
| Ser | Ala | Tyr | Met | Cys | Thr | Pro | Ser | Gly | Ser | Met | Val | Ser | Ser | Asp | Thr |
| | | | 290 | | | | | 295 | | | | | 300 |
| Gln | Leu | Phe | Asn | Arg | Pro | Phe | Trp | Leu | Gln | Arg | Ala | Gln | Gly | Lys | Asn |
| 305 | | | | | 310 | | | | | 315 | | | | | 320 |
| Asn | Gly | Val | Cys | Trp | Asn | Asn | Glu | Leu | Phe | Val | Ser | Ile | Val | Asp | Asn |
| | | | 325 | | | | | 330 | | | | | 335 |
| Thr | Arg | Gly | Thr | Asn | Leu | Ser | Ile | Ser | Val | Lys | Arg | Asp | Gly | Glu | Pro |
| | | | 340 | | | | | 345 | | | | | 350 |
| Leu | Gly | Lys | Gln | Ser | Lys | Tyr | Lys | Ala | Glu | Asp | Phe | Lys | Gln | Tyr | Val |
| | | | 355 | | | | | 360 | | | | | 365 |
| Arg | His | Cys | Glu | Ile | Phe | Asp | Val | Ser | Leu | Val | Leu | Gln | Leu | Gly | Arg |
| | | | 370 | | | | | 375 | | | | | 380 |
| Val | Pro | Leu | Thr | Ala | Glu | Ala | Val | Ala | His | Leu | Asn | Ala | Met | Asp | Pro |
| 385 | | | | | 390 | | | | | 395 | | | | | 400 |

```
                                      -continued

Asp Ile Leu Arg Gly Trp Asn Ile Gly Phe Gln Ala Ala Ala Pro Val
            405                 410                 415

Ser Gly Glu Glu Asn Tyr Arg Tyr Leu Ser Ser Leu Ala Thr Lys Cys
            420                 425                 430

Pro Asp Ile Pro Pro Ala Glu Val Pro Lys Ser Arg Tyr Asp Gly Met
        435                 440                 445

Ser Phe Trp Thr Ile Asp Val Ser Lys Ser Leu Thr Ala Asp Leu Asp
        450                 455                 460

Asn Tyr Thr Leu Gly Arg Lys Phe Leu Tyr Gln Ala Gly Leu Ser Thr
465                 470                 475                 480

Arg Gly Ser Thr Thr Gly Arg Lys Arg Arg Ala Ser Pro Ala Ile Ser
                485                 490                 495

Arg Ser Lys Gly Lys Arg Arg Thr Lys Gln
            500                 505
```

DIAGNOSING AND PROTECTING AGAINST TURSIOPS TRUNCATUS PAPILLOMAVIRUS

TECHNICAL FIELD

The presently-disclosed subject matter relates to diagnosis and prevention of papillomavirus infections in marine mammals, and, more particularly, to diagnosis and prevention of papillomavirus infections in dolphins.

BACKGROUND

The worldwide prevalence of PV-infection in humans is very high. Indeed, human PVs (HPVs) are the most frequently sexually transmitted viruses of the world. See Garland, S. M. 2002. *Pathology* 34:213-224, which is incorporated herein my reference. Whereas nearly 100 HPV types have been described, an intensive search for animal PVs has just begun.

After infection of the basal cells of cutaneous or mucosal skin, these small DNA viruses start to induce an increased epithelial proliferation in the course of which they show a strong host- and tissue-specificity. See zur Hausen, H., and E. M. de Villiers. 1994. *Annual review of microbiology* 48:427-447, which is incorporated herein by this reference. A hyperproliferation of the suprabasal cells, such as the development of warts, papillomas, or condylomas, is induced by viral protein activity interfering with the pathways of cellular tumor suppressor proteins. See Chow, L. T., and T. R. Broker. 1994. *Intervirology* 37:150-158; and Howley, P. M., and D. R. Lowy. 2001. *Fields Virology*. 4th edition. Raven Press, Philadelphia. 2197-2229, which are incorporated herein by reference. These primarily benign tumors (warts, condylomas, papillomas) frequently disappear due to a cell-mediated immune response; however, some PVs contribute to malignant progression of the epithelial tumors.

In humans, 10-30% of PV-induced severe neoplasia lead to an invasive cervical carcinoma, the second most frequent cancer of women worldwide. See Einstein, M. H., and G. L. Goldberg. 2002. *Cancer Investigation* 20:1080-1085; and Walboomers, J. M., et al. 1999. *The Journal of Pathology* 189:12-19, which are incorporated herein by reference. Cervical carcinoma is believed to be entirely attributable to PV-infections and represents the most common cause of cancer mortality in women in developing countries. See Parkin, D. 2005. Presented at the 22nd International Papillomavirus Conference, Vancouver, Canada, April 30-May 6. Title: World Burden of Infection-associated Cancers; and Eder, P., I. et al. 2005. Presented at the 22nd International Papillomavirus Conference, Vancouver, Canada, April 30-May 6. Title: A new HPV DNA Test for Developing Countries, which are incorporated herein by reference. Those PVs, which demonstrate a stronger oncogenic potential are classified as high risk viruses, and can be found amongst oral, genital, and cutaneous types.

PVs have been isolated from marine mammals, including one PV isolated from skin lesions of a species of the Sirenia order, a captive Florida manatee (*Trichechus manatus latirostris* PV-1, TmPV-1), and from genital lesions of a species of the Cetacea order, free-ranging and captive Atlantic bottlenose dolphin (*Tursiops truncates*). See Bossart, G. D., R. Y. Ewing, M. Lowe, M. Sweat, S. J. Decker, C. J. Walsh, S. J. Ghim, and A. B. Jenson. 2002. *Experimental and Molecular Pathology* 72:37-48; Rector, A., G. D. Bossart, S. J. Ghim, J. P. Sundberg, A. B. Jenson, and M. Van Ranst. 2004. *Journal of Virology* 78:12698-12702; and Rehtanz, M., S.-J. Ghim, A. Rector, M. Van Ranst, P. A. Fair, G. D. Bossart, and A. B. Jenson. 2006. *Journal of General Virology* 87:3559-3565, which are incorporated herein by reference. With respect to cetaceans, PVs have been found in or suspected to be the agents of: genital and/or lingual tumors in Burmeister's porpoises (*Phocoena spinipinnis*, PsPV-1), and dusky dolphins (*Lagenorhynchus obscurus*) from Peru; cutaneous warts in a harbour porpoise (*Phocoena phocoena*) of the North Sea, and at least one killer whale (*Orcinus orca*, "Keiko"—captured in the North Atlantic 1983); and genital warts of sperm whales (*Physeter catodon*) from Icelandic waters, and of bottlenose (*Tursiops truncatus*) and long-beaked common dolphins (*Delphinus capensis*) from Peru.

The first evidence of virus-like particle (VLP)-vaccine efficacy came from a canine oral PV (COPV) system. Beagles vaccinated with VPLs generated in insect cells became completely resistant to experimental challenges with COPV. Virus-like particles (VLPs) derived from HPV-16 and -18 and used as PV vaccines have been generated in insect cells [CERVARIX™, GlaxoSmithKline (GSK), Biologicals of Rixensart, Belgium]. Similar particles derived from HPV-6, -11, -16, and -18 have been prepared for a quadrivalent vaccine in yeast (GARDASIL®, Merck & Co. of Rahway; N.J.). HPV-16 and -18 represent the most prevalent human high-risk genital PVs, together accounting for approximately 72% of cervical carcinomas, whereas HPV-6 and -11 are representatives for low-risk viruses, which cause warts in both sexes. The HPV VLP vaccines consist of the corresponding self-assembled major capsid proteins, the L1 proteins. In first trials with more than 3,000 participants involved, both vaccines prevented persistent infection of the viral types included in the vaccine for 100% of vaccinated women, and reduced cervical abnormalities by more than 90%.

A high incidence of orgenital papillomas and squamous cell carcinomas have been documented in free-ranging and captive dolphins. See Bossart, G. D., S. J. Ghim, M. Rehtanz, J. D. Goldstein, R. A. Varela, R. Ewing, P. A. Fair, R. Lenzi, B. Joseph, C. Hicks, L. Schneider, C. J. McKinnie, J. S. Reif, R. Sanchez, A. Lopez, S. Novoa, J. Bernal, M. Goretti, M. Rodriguez, R. H. Defran, and A. B. Jenson. 2005. *Aquatic Mammals* 31:473-480, which is incorporated herein by reference. Surgical removal of lingual and genital dolphin warts from captive animals is almost always associated with recurrence. Additionally, some of these tumors, which are believed to be caused by PVs, become malignant and spread into the brain. Accordingly, there remains a need in the art for compositions and methods for preventing or reducing transmission of TtPVs between dolphins held in the same pools (horizontal transmission) and between mothers and calves (vertical transmission).

SUMMARY

The presently-disclosed subject matter meets some or all of the above-identified needs, as will become evident to those of ordinary skill in the art after a study of information provided in this document. This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes isolated nucleic acid molecules, isolated amino acid molecules, immunogenic compositions, and methods related to diagnosing and protecting against *Tursiops truncatus* papillomavirus (TtPV).

In certain embodiments, isolated nucleic acid molecules of the presently-disclosed subject matter include an isolated nucleic acid molecule having at least about 80% homology, at least about 85% homology, at least about 90% homology, or at least about 95% homology to the nucleic acid sequence of an L1 gene of *Tursiops truncates* papillomavirus type 2 (TtPV-2), as set forth in SEQ ID NO: 1.

In certain embodiments, isolated polypeptides of the presently-disclosed subject matter include a polypeptide encoded by a nucleic acid molecule having at least about 80% homology, at least about 85% homology, at least about 90% homology, or at least about 95% homology to the nucleic acid sequence as set forth in SEQ ID NO: 1. In certain embodiments, isolated polypeptides of the presently-disclosed subject matter include a polypeptide having at least about 80% homology, at least about 85% homology, at least about 90% homology, or at least about 95% homology to the amino acid sequence as set forth in SEQ ID NO: 2.

In certain embodiments, isolated nucleic acid molecules of the presently-disclosed subject matter include an isolated nucleic acid molecule having at least about 80% homology, at least about 85% homology, at least about 90% homology, or at least about 95% homology to the nucleic acid sequence of an L1 gene of *Tursiops truncates* papillomavirus type 1 (TtPV-1), as set forth in SEQ ID NO: 3.

In certain embodiments, isolated polypeptides of the presently-disclosed subject matter include a polypeptide encoded by a nucleic acid molecule having at least about 80% homology, at least about 85% homology, at least about 90% homology, or at least about 95% homology to the nucleic acid sequence as set forth in SEQ ID NO: 3. In certain embodiments, isolated polypeptides of the presently-disclosed subject matter include a polypeptide having at least about 80% homology, at least about 85% homology, at least about 90% homology, or at least about 95% homology to the amino acid sequence as set forth in SEQ ID NO: 4.

The presently-disclosed subject matter includes an immunogenic composition for conferring protection against *Tursiops truncatus* papillomavirus (TtPV) infection in a subject susceptible to TtPV infection. In certain embodiments, the immunogenic composition includes a virus-like particle assembled from a TtPV L1 protein, for example, a TtPV L1 protein from TtPV-1, TtPV-2, or TtPV-3. In certain embodiments, the immunogenic compositions includes virus-like particles assembled from two or more TtPV L1 proteins, for example, from TtPV-1, TtPV-2, and/or TtPV-3.

In certain embodiments, the immunogenic composition includes a virus-like particle assembled from a polypeptide encoded by a nucleic acid molecule having at least about 80% homology, at least about 85% homology, at least about 90% homology, or at least about 95% homology to the nucleic acid sequence as set forth in SEQ ID NO: 1. In certain embodiments, the immunogenic composition includes a virus-like particle assembled from a polypeptide having at least about 80% homology, at least about 85% homology, at least about 90% homology, or at least about 95% homology to the amino acid sequence as set forth in SEQ ID NO: 2. In certain embodiments, the immunogenic compositions include an adjuvant.

In certain embodiments, the immunogenic composition includes a virus-like particle assembled from a polypeptide encoded by a nucleic acid molecule having at least about 80% homology, at least about 85% homology, at least about 90% homology, or at least about 95% homology to the nucleic acid sequence as set forth in SEQ ID NO: 3. In certain embodiments, the immunogenic composition includes a virus-like particle assembled from a polypeptide having at least about 80% homology, at least about 85% homology, at least about 90% homology, or at least about 95% homology to the amino acid sequence as set forth in SEQ ID NO: 4. In certain embodiments, the immunogenic compositions include an adjuvant.

The presently-disclosed subject matter includes methods of protecting a subject susceptible to TtPV infection against TtPV infection. In certain embodiments, methods of protecting the subject against TtPV infection include administering to the subject susceptible to TtPV infection an immunogenic composition including a virus-like particle assembled from a TtPV L1 protein, for example, a TtPV L1 protein from TtPV-1, TtPV-2, or TtPV-3. In certain embodiments, methods of protecting the subject against TtPV infection include administering to the subject an immunogenic composition including virus-like particles assembled from two or more TtPV L1 proteins, for example, from at least two TtPV L1 proteins selected from: TtPV-1, TtPV-2, and TtPV-3.

In certain embodiments, methods of protecting the subject against TtPV infection include administering to the subject an immunogenic composition including a virus-like particle assembled from a polypeptide encoded by a nucleic acid molecule having at least about 80% homology, at least about 85% homology, at least about 90% homology, or at least about 95% homology to the nucleic acid sequence as set forth in SEQ ID NO: 1.

In certain embodiments, methods of protecting the subject against TtPV infection include administering to the subject an immunogenic composition including a virus-like particle assembled from a polypeptide having at least about 80% homology, at least about 85% homology, at least about 90% homology, or at least about 95% homology to the amino acid sequence as set forth in SEQ ID NO: 2.

In certain embodiments, methods of protecting the subject against TtPV infection include administering to the subject an immunogenic composition including a virus-like particle assembled from a polypeptide encoded by a nucleic acid molecule having at least about 80% homology, at least about 85% homology, at least about 90% homology, or at least about 95% homology to the nucleic acid sequence as set forth in SEQ ID NO: 3.

In certain embodiments, methods of protecting the subject against TtPV infection include administering to the subject an immunogenic composition including a virus-like particle assembled from a polypeptide having at least about 80% homology, at least about 85% homology, at least about 90% homology, or at least about 95% homology to the amino acid sequence as set forth in SEQ ID NO: 4.

In certain embodiments, methods of protecting the subject against TtPV infection include administering to the subject susceptible to TtPV infection an immunogenic composition including VLPs assembled from a TtPV L1 protein, and an adjuvant. The presently-disclosed subject matter includes methods of diagnosing TtPV infection in a subject. In certain embodiments, methods of diagnosing TtPV in the subject include providing a virus-like particle assembled from at least one TtPV L1 protein; contacting the virus-like particle with serum obtained from the subject; and identifying the subject as having TtPV infection if a TtPV antibody capable of binding the virus-like particle is detected in the serum. In certain embodiments, the binding is detected using an antibody capable of binding the TtPV antibody. In some embodiments the virus-like particle is immobilized on a substrate, such as an ELISA plate.

BRIEF DESCRIPTION OF THE DRAWINGS

FIGS. 8A-8C are transmission electron microscopy pictures of negatively-stained, purified TtPV-1;

FIGS. 9A and 9B are transmission electron microscopy pictures of negatively-stained, purified TtPV-2;

FIG. 10 depicts a sodium dodecyl sulfate polyacrylamide gel (SDS-PAGE) showing purified and concentrated IgG from combined serum of two different free-ranging dolphins not showing any sign of a disease or infection, where lanes 5 and 6 show the diluted serum, and lanes 1 to 4 show dilutions of the purified and concentrated dolphin-IgG; and FIG. 11 is a table depicting the results of an ELISA study, where ELISA plates are coated with purified intact TtPV VLPs (A and C), or denatured TtPV VLPs (B and D).

BRIEF DESCRIPTION OF THE SEQUENCE LISTING

Figure 1:
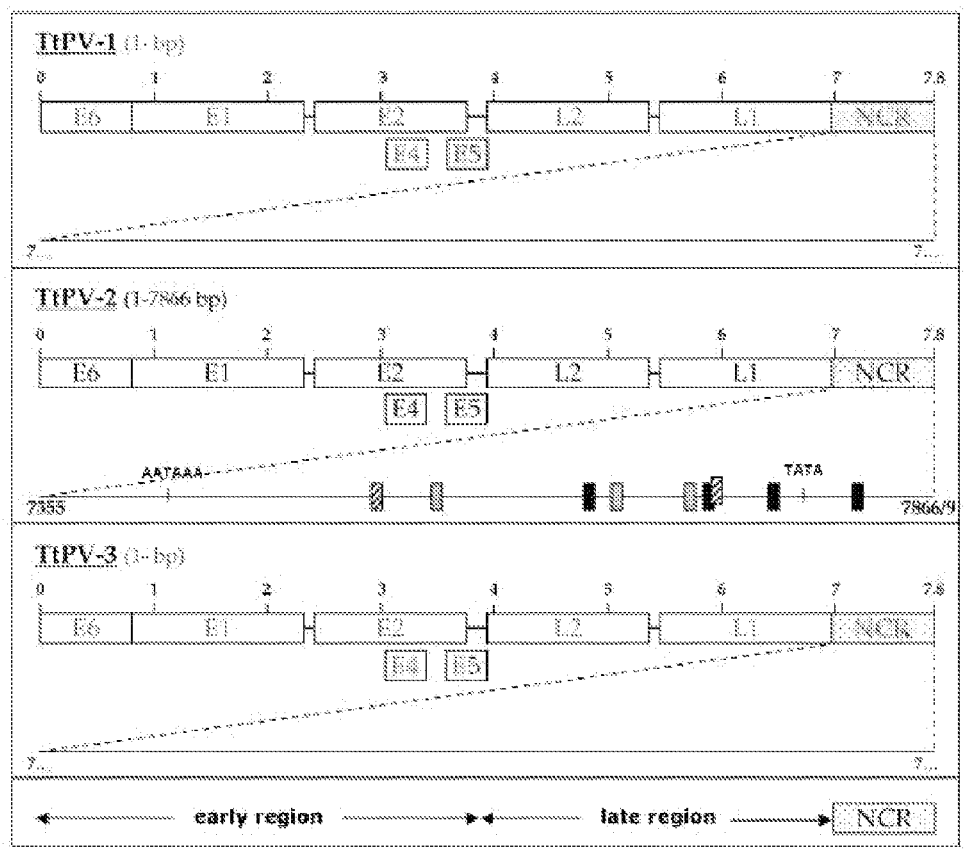
FIG. 1 is a schematic presentation of the genome organization of TtPV-1, -2, and -3, including the open reading frames (ORFs) and the non-coding regions (NCRs), where the distribution of consensus E2 binding sites (E2-BS, black boxes), putative E1-BS (dark grey boxes), and putative BS for transcriptional regulators such as SP1 (striped boxes) and NF1 (light grey boxes) as well as perfect TATA-boxes and polyadenylation signal sites are depicted.

SEQ ID NO: 1 is the nucleic acid sequence of an L1 gene of *Tursiops truncates* papillomavirus type 2 (TtPV-2);

SEQ ID NO: 2 is the amino acid sequence of an L1 protein of *Tursiops truncates* papillomavirus type 2 (TtPV-2);

SEQ ID NO: 3 is the nucleic acid sequence of an L1 gene of *Tursiops truncates* papillomavirus type 1 (TtPV-1); and SEQ ID NO: 4 is the amino acid sequence of an L1 protein of *Tursiops truncates* papillomavirus type 1 (TtPV-1).

DESCRIPTION OF EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described. While the following terms are believed to be well understood by one of ordinary skill in the art, the following definitions are set forth to facilitate explanation of the presently-disclosed subject matter.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The term "associated with", and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

As used herein, the term "biologically active" refers to an ability to affect treatment for the disease state being treated when provided in an effective amount.

The terms "coding sequence" and "open reading frame" (ORF) are used interchangeably and refer to a nucleic acid sequence that is transcribed into RNA such as mRNA, rRNA, tRNA, snRNA, sense RNA, or antisense RNA. In some embodiments, the RNA is then translated in vivo or in vitro to produce a polypeptide.

As used herein, the term "effective amount" refers to a dosage sufficient to provide treatment for the disease state being treated. The exact amount that is required will vary from subject to subject, depending on the species, age, and general condition of the subject, the particular adjuvant being used, mode of administration, and the like. As such, the effective amount will vary based on the particular circumstances, and an appropriate effective amount can be determined in a particular case by one of ordinary skill in the art using only routine experimentation.

The term "expression vector" refers to a bacteriophage, a plasmid, or another like agent, containing an expression cassette, comprising a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

Typically, however, the expression cassette is heterologous with respect to the host; i.e., the particular DNA sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus.

The term "fragment" refers to a nucleic acid or amino acid sequence that comprises a subset of another nucleic acid or amino acid sequence. A fragment of a nucleic acid sequence can be any number of nucleotides that is less than that found in another nucleic acid sequence, and thus includes, but is not limited to, the sequences of an exon or intron, a promoter, an enhancer, an origin of replication, a 5' or 3' untranslated region, a coding region, and a polypeptide binding domain. It is understood that a fragment can also comprise less than the entirety of a nucleic acid sequence, for example, a portion of an exon or intron, promoter, enhancer, etc. Similarly, a fragment of an amino acid sequence can be any number of residues that is less than that found in a naturally occurring polypeptide, and thus includes, but is not limited to, domains, features, repeats, etc. Also similarly, it is understood that a fragment of an amino acid sequence need not comprise the entirety of the amino acid sequence of the domain, feature, repeat, etc. A fragment can retain one or more of the biological activities of the a naturally occurring polypeptide. In some embodiments, a fragment can comprise a domain or feature, and optionally additional amino acids on one or both sides of the domain or feature.

A fragment can also be a "functional fragment," in which the fragment retains a specific biological function of the nucleic acid sequence or amino acid sequence of interest.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The terms "heterologous", "recombinant", and "exogenous", when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides. A "homologous" nucleic acid (or amino acid) sequence is a nucleic acid (or amino acid) sequence naturally associated with a host cell into which it is introduced.

The term "isolated", when used in the context of an isolated nucleic acid molecule or an isolated polypeptide, is a nucleic acid molecule or polypeptide that, by the hand of man, exists apart from its native environment and is therefore not a product of nature. An isolated nucleic acid molecule or polypeptide can exist in a purified form or can exist in a non-native environment such as, for example, in a transgenic host cell.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) *Nucleic Acid Res* 19:5081; Ohtsuka et al. (1985) *J Biol Chem* 260: 2605-2608; Rossolini et al. (1994) *Mol Cell Probes* 8:91-98). The terms "nucleic acid" or "nucleic acid sequence" can also be used interchangeably with gene, open reading frame (ORF), cDNA, and mRNA encoded by a gene.

The terms "polypeptide", "protein", and "peptide", which are used interchangeably herein, refer to a polymer of the 20 protein amino acids, or amino acid analogs, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The term "transformation" refers to a process for introducing heterologous DNA into a cell. Transformed cells are understood to encompass not only the end product of a transformation process, but also transgenic progeny thereof.

The presently-disclosed subject matter includes isolated nucleic acid molecules, isolated amino acid molecules, compositions, and methods related to diagnosing and protecting against *Tursiops truncatus* papillomavirus (TtPV).

A schematic presentation of the TtPV genome is shown in FIG. 1. The PV genes and associated proteins can be classified with respect to their chronological appearance during the viral life cycle. In this regard, they can be classified as early (E) and late (L), early referring to a time before replication of the virus has begun, and late referring to a time after replication of the virus has begun. All TtPVs, including TtPV type 1 (TtPV-1), TtPV type 2 (TtPV-2), and TtPV type 3 (TtPV-3), contain at least five open reading frames (ORFs): E6, E1, E2, L2, L1; and two putative genes: E4 and E5, whereas they all lack an E7 ORF. PVs contain a covalently-closed circular DNA double strand with ORFs located on the coding strand. Products of late (L) genes represent the structural capsid proteins, whereas products of the two early (E) genes fulfill regulatory tasks during cell transformation, replication, and transcription. In between the ORFs of L1 and E6, a non-coding region (NCR) is located, which contains cis-control elements for regulating transcription and replication of the viral genome.

The presently-disclosed subject matter includes an isolated nucleic acid molecule having at least about 80% homology, at least about 85% homology, at least about 90% homology, or at least about 95% homology to the nucleic acid sequence of an L1 gene of *Tursiops truncates* papillomavirus type 2 (TtPV-2), as set forth in SEQ ID NO: 1.

The presently-disclosed subject matter includes an isolated biologically active polypeptide encoded by a nucleic acid molecule having at least about 80% homology, at least about 85% homology, at least about 90% homology, or at least about 95% homology to the nucleic acid sequence of an L1 gene of *Tursiops truncates* papillomavirus type 2 (TtPV-2), as set forth in SEQ ID NO: 1.

The presently-disclosed subject matter includes an isolated biologically active polypeptide having at least about 80% homology, at least about 85% homology, at least about 90% homology, or at least about 95% homology to the amino acid sequence for an L1 protein of *Tursiops truncates* papillomavirus type 2 (TtPV-2), as set forth in SEQ ID NO: 2.

The presently-disclosed subject matter includes an isolated nucleic acid molecule having at least about 80% homology, at least about 85% homology, at least about 90% homology, or at least about 95% homology to the nucleic acid sequence of an L1 gene of *Tursiops truncates* papillomavirus type 1 (TtPV-1), as set forth in SEQ ID NO: 3.

The presently-disclosed subject matter includes an isolated biologically active polypeptide encoded by a nucleic acid molecule having at least about 80% homology, at least about 85% homology, at least about 90% homology, or at least about 95% homology to the nucleic acid sequence of an L1 gene of *Tursiops truncates* papillomavirus type 1 (TtPV-1), as set forth in SEQ ID NO: 3.

The presently-disclosed subject matter includes an isolated biologically active polypeptide having at least about 80% homology, at least about 85% homology, at least about 90% homology, or at least about 95% homology to the amino acid sequence for an L1 protein of *Tursiops truncates* papillomavirus type 1 (TtPV-1), as set forth in SEQ ID NO: 4.

The presently-disclosed subject matter includes immunogenic compositions and vaccines comprising virus-like particles (VLPs) assembled from an L1 protein of at least one type of *Tursiops truncatus* papillomavirus (TtPV). In certain embodiments, L1-VLPs of one type of TtPV are provided, e.g., L1-TtPV-1, L1-TtPV-2, or L1-TtPV-3. In other embodiments, L1-VLPs of multiple types can be provided, which compositions can be used as polyvalent vaccines.

As used herein, an L1 protein of a TtPV refers to a full-length L1 protein, or a functional fragment thereof. For example, in certain embodiments, a full-length L1 protein of TtPV-2 (SEQ ID NO: 2) can be used. For another example, in certain embodiments, a functional fragment of the L1 protein of TtPV-2 can be used. Exemplary functional fragments of the L1 protein of TtPV-2 include, for example, fragments of the L1 protein wherein up to about 26 amino acids are removed from the C-terminus, up to about 20 amino acids are removed from the C-terminus, up to about 15 amino acids are removed from the C-terminus, up to about 10 amino acids are removed from the C-terminus, up to about 5 amino acids are removed from the C-terminus, or about 1 amino acid is removed from the C-terminus, relative to the full-length L1 protein. Also, as used herein, an L1 protein of a TtPV refers to an isolated biologically active polypeptide encoded by a nucleic acid molecule having at least about 80% homology, at least about 85% homology, at least about 90% homology, or at least about 95% homology to the nucleic acid sequence as set forth in SEQ ID NO: 1. Also, as used herein, an L1 protein of a TtPV refers to an isolated biologically active polypeptide having at least about 80% homology, at least about 85% homology, at least about 90% homology, or at least about 95% homology to the amino acid sequence for an L1 protein of *Tursiops truncates* papillomavirus type 2 (TtPV-2), as set forth in SEQ ID NO: 2.

For another example, in certain embodiments, a full-length L1 protein of TtPV-1 (SEQ ID NO: 4) can be used. For another example, in certain embodiments, a functional fragment of the L1 protein of TtPV-1 can be used. Exemplary functional fragments of the L1 protein of TtPV-1 include, for example, fragments of the L1 protein wherein up to about 26 amino acids are removed from the C-terminus, up to about 20 amino acids are removed from the C-terminus, up to about 15 amino acids are removed from the C-terminus, up to about 10 amino acids are removed from the C-terminus, up to about 5 amino acids are removed from the C-terminus, or about 1 amino acid is removed from the C-terminus, relative to the full-length L1 protein. Also, as used herein, an L1 protein of a TtPV refers to an isolated biologically active polypeptide encoded by a nucleic acid molecule having at least about 80% homology, at least about 85% homology, at least about 90% homology, or at least about 95% homology to the nucleic acid sequence as set forth in SEQ ID NO: 3. Also, as used herein, an L1 protein of a TtPV refers to an isolated biologically active polypeptide having at least about 80% homology, at least about 85% homology, at least about 90% homology, or at least about 95% homology to the amino acid sequence for an L1 protein of *Tursiops truncates* papillomavirus type 1 (TtPV-1), as set forth in SEQ ID NO: 4.

Figure 2:
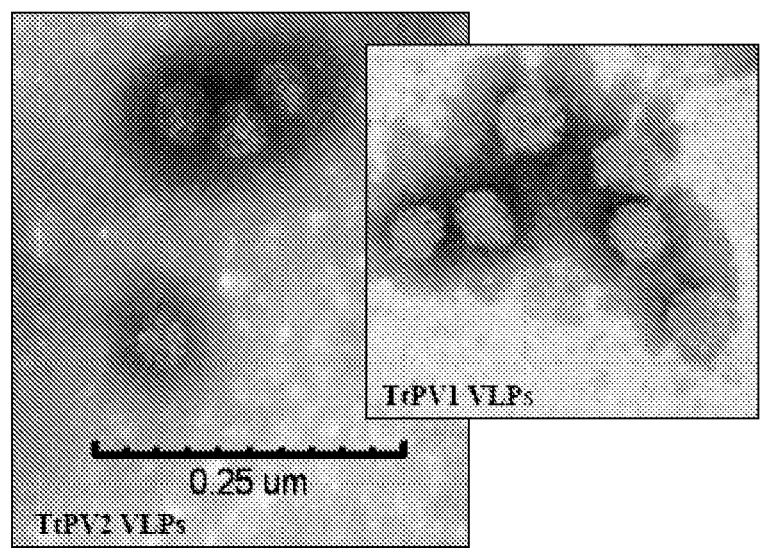
FIG. 2 includes transmission electron microscopy pictures of negatively stained, purified TtPV-1 and TtPV-2 VLPs.

An exemplary process for preparing TtPV L1 virus like particles (VLPs) makes use of an expression system including an expression vector and an appropriate host cell. The expression vector includes a TtPV L1 nucleotide sequence capable of encoding TtPV L1 protein of interest. For example, when the protein of interest is the TtPV-2 L1 protein, the expression vector can include the nucleotide sequence of SEQ ID NO: 1, or a fragment thereof, which is capable of encoding a TtPV-2 L1 protein (full length or functional fragment). For another example, when the protein of interest is the TtPV-1 L1 protein, the expression vector can include the nucleotide sequence of SEQ ID NO: 3, or a fragment thereof, which is capable of encoding a TtPV-1 L1 protein (full length or functional fragment). The host cell is infected with the vector. Recombinant L1 proteins are generated and self-assemble into VLPs in the host cell. The resulting VLPs are isolated and purified. With reference to FIG. 2, transmission electron microscopy pictures of prepared L1-VLPs of TtPV display the presence of single capsomers and indicate that L1 proteins assemble into particles of about 50 to 60 nm.

Additional information related to methods of producing PV proteins of interest and VLPs, including PV L1 proteins and VLPs, can be found in Examples presented in this document, and in the following references, each of which is incorporated herein by reference: U.S. Pat. Nos. 5,057,411; 5,874,089; 6,485,728; 6,887,478; 7,001,995; 6,908,615; 6,165,471; and 6,153,201; and United States Patent Application Publication Nos. 2002/0197264; 2004/0086527; 2005/0026257; 2006/0029612; and 2005/0282263.

In certain embodiments, the compositions and vaccines can include VLPs assembled from at least one TtPV L1 protein provided in a pharmaceutically-acceptable formulation. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The compositions can take such forms as suspensions, solutions, or emulsions in oily or aqueous vehicles, and can contain formulatory agents such as suspending, stabilizing and/or dispersing agents. The formulations can be presented in unit-dose or multi-dose containers, for example sealed ampoules and vials, and can be stored in a frozen or freeze-dried (lyophilized) condition requiring only the addition of sterile liquid carrier immediately prior to use.

In certain embodiments, the compositions can include VLPs assembled from at least one TtPV L1 protein, and an adjuvant. Suitable adjuvants for use in the practice of the present subject matter include, but are not limited to (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., *Proc. Natl. Acad. Sci., USA*, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, (5) cytokines, (6) aluminum hydroxide or aluminum phosphate, (7) other adjuvants discussed in any document cited and incorporated by reference into this document, or (8) any combinations or mixtures thereof.

The presently-disclosed subject matter includes a method of protecting a subject against TtPV infection by administering VLPs assembled from at least one TtPV L1 protein. In certain embodiments, method can include protecting a subject against TtPV infection by administering a composition or vaccine, as described above. As used herein, the term "subject" includes any animal capable of being infected by TtPV.

The presently-disclosed subject matter includes a method for diagnosing TtPV infection in a subject In certain embodiments, the method includes providing a TtPV L1-VLP; contacting the TtPV L1-VLP with serum obtained from the subject; and identifying the subject as having TtPV infection if an antibody capable of binding the TtPV L1-VLP is detected in the serum.

Binding between L1-VLPs can be detected using a tagged-antibody capable of binding to the VLP antibody. Alternatively, binding between L1-VLPs can be detected using a series of antibodies, wherein at least one antibody in the series binds to the VLP antibodies, and at least one antibody in the series is tagged for detection. For example, an appropriate series of antibodies can include a primary antibody capable of binding the VLP antibody, and a secondary antibody capable of binding the primary antibody, which secondary antibody is tagged to allow for detection, e.g., fluorescent, radioactive, etc.

In certain embodiments, the method includes providing a TtPV L1-VLP immobilized on a substrate; for example, an ELISA plate (Dynatech Laboratories, Inc., Chantilly, Va.) can be coated with L1-VLPs of at least one type of TtPV. In certain embodiments, L1-VLP of different types of TtPV can be immobilized on a substrate in an organized manner, such that diagnosis of individual and/or multiple types of TtPV can be readily made, as will be understood by those of ordinary skill in the art upon reviewing this document. In certain embodiments, various controls can be provided, which can be desirable for use in comparing binding detection results for test serum, as will be understood by those of ordinary skill in the art upon reviewing this document. Additional information related to methods for diagnosing TtPV can be found in Examples presented in this document, and information related to detecting antibody/PV L1-Protein binding can be found in U.S. Pat. Nos. 6,887,478; 6,485,728; and 5,874,089, which are incorporated herein by reference.

The presently-disclosed subject matter is further illustrated by the following specific but non-limiting examples. The following examples may include compilations of data that are representative of data gathered at various times during the course of development and experimentation related to the present invention.

EXAMPLES

Example 1

Dolphin Sera and Lesion Materials

Sera and lesions from free-ranging dolphins were collected. Combined Serum of free-ranging dolphins not showing any physical signs of viral infections or diseases served to induce alpha-dolphin-immunoglobulin G (IgG)-antibody production in rabbits as a negative control to use in ELISA studies and further analyses. IgG was purified using Protein A-Sepharose (Sigma, St. Louis, Mo.) and concentrated using CENTRICON® plus filter devices with Ultracel PL membranes (Millipore, Billerica, Mass.) according to the manufacturer's recommendations.

Example 2

DNA Extraction

Tissue biopsies were finely minced with a scalpel and digested overnight at 55° C. in digestion buffer (10 mM Tris, 0.5% SDS, pH 7.4) containing 500 µg proteinase K. Deproteinization is performed by phenol-, phenol-chloroform-isoamylalcohol-, and chloroform-extractions followed by ethanol precipitation to recover DNA. Air-dried DNA-pellets are then resuspended in 20-50 µl TE-buffer (10 mM Tris-HCl, 1 mM EDTA, pH 8.0).

Example 3

Isothermal, Multiply Primed RCA

To amplify PV-DNA isolated from lesion tissues a rolling-circle-amplification (RCA) was carried out with the TempliPhi™ 100 Amplification Kit (Amersham Biosciences, Roosendaal, The Netherlands) following the manufacturer's instructions using 1-2 μl of extracted DNA and adding 450 μM extra dNTPs as previously described in Rector, et al. 2004 *Journal of Virology* 78:12698-12702, which is incorporated herein by reference. Restriction enzyme-digested amplified products were then examined in agarose gels, and right-sized products of about 8 kb were cloned and sequenced.

Example 4

DNA Cloning and Sequencing

The entire isolated, RC-amplified TtPV genomes of different types were cloned into pUC18 or pUC19 via appropriate restriction sites (e.g., BamHI (located in L1 of type 1); one EcoRI (located twice in E1 of type 2)). The genomes were sequenced using transposon integrations with the EZ::TN <KAN-2> Insertion Kit (Epicentre, Madison, Wis., USA) according to the manufacturer's protocol. Twenty-four to 32 colonies representing the same number of integration sites were sequenced forward and backward. The TtPV-1 and -3 sequences are put together using appropriate software and the TtPV-2 sequence is put together using the DNASTAR Lasergene SeqMan software (version 5.52). To recover the loss of 152 bp within the E1 ORF of TtPV-2 between the first and the second EcoRI site during the cloning procedure, the corresponding original RCA-product served as the original template in a conventional PCR using TtPV-2 E1 specific primers. The resulting additional cloned sequence was then integrated into the sequence obtained by using the transposon integrations.

Example 5

DNA and Protein Sequence Analysis

ORFs are identified using MacVector (version 7.2), and nucleotide and protein sequence similarities were searched via the NCBI BLAST server. Sequence alignments and the Phylogeny were calculated with DNASTAR Lasergene SeqMan, ClustalW, GENEDOC and MEGA3.

Example 6

VLP Production

Using cloned complete TtPV templates, the corresponding L1 genes encoding the L1 proteins were amplified using PCR. The following primers were used: forward primers 5'-ATGCTCGAGATGCTGCATATACCA-3' (TtPV-1) and 5'-CCGCTC-GAGATGCTGCAGCTGCCTCC-3' (TtPV-2); and reverse primers 5'-ATGAAGC-TTTTACTGTTTAG-TACGCCT-3' (TtPV-1) and 5'-CCCAAGCTTTTAGG-TACG-TGTCACCTTCC-3' (TtPV-2) containing XhoI (forward) and HindIII (reverse) restriction sites (italicized).

The XhoI-HindIII fragment was then isolated and separately inserted into the multiple cloning site of the baculoviral transfer vector pBlueBac4.5 (Invitrogen, Carlsbad, Calif., USA) downstream of the polyhedrin promoter. TtPV-1 and -2-recombinant baculovirus vectors were prepared using the Bac-N-Blue Kit (Invitrogen, Carlsbad, Calif., USA), according to the manufacturer's instructions, to transfect *Spodoptera frugiperda* Sf9 cells as described in Ghim, S. et al. 2004 *Biochemical and Biophysical Research Communications* 324:1108-1115, which is incorporated herein by reference.

The insect cells were cultured in supplemented Grace's medium (Gibco/BRL, Gaithersburg, Md., USA) containing 10% fetal bovine serum and 3.6 mM Glutamine. Using Seaplaque GTG agarose (BioWhitaker, Rockland, Me., USA), positive recombinant baculoviruses were plaque-purified and subsequently tested in polyhedrin-specific PCRs for the presence of the L1-genes.

Example 7

VLP Purification

Seventy-two hrs post infection, Sf9 or Sf21 insect cells were harvested and processed for VLP purification. Briefly, cells were pelleted by centrifugation (170 g, 10 min, 4° C.) and diluted in Dulbecco's Phosphate-Buffered Saline (DPBS), Gibco/BRL (Gaithersburg, Md., USA). After dounce homogenization and sonication, 2×CsCl/DPBS was added with a final CsCl density of 1.33 g/cm$^3$, which was confirmed by measuring the refractive index. After differential ultracentrifugation at 45,000 g for 18 hrs at 4° C., bands of correct density containing the VLPs were collected and dialyzed in dialysis cassettes (Slide-A-Lyzer®, Pierce, Rockford, Ill., USA) at 4° C. against 500× the amount of DPBS buffer for 30 min and with exchanged buffer for another 2 hrs. The final dialysis was then performed for 24-48 hrs in fresh DPBS buffer at 4° C. Expression of the corresponding L1 genes was identified using purified VLPs in sodium dodecyl sulfate polyacrylamide gels (SDS-PAGE) and subsequent immunoblotting. A negative staining with 1.5-2% tungstophosphoric acid (pH 6.8) of the purified VLPs was carried out to confirm that the self-assembled VLPs had icosahedral symmetry, and that their characteristic size by transmission electron microscopy (Philips CM12 Transmission Electron Microscope, University of Louisville, Louisville, Ky., USA).

Example 8

SDS-PAGE and Immunoblotting

Combined dolphin serum, as well as purified and concentrated dolphin-IgG, was diluted and 1 μl of each dilution loaded onto a 10% sodium dodecyl sulfate polyacrylamide gel (SDS-PAGE). The staining was carried out with Coomassie brilliant blue. For the VLP Western Blot, the concentrations of the purified VLPs were determined by Bradford assay. Bradford, M. 1976 *Analytical biochemistry* 72: 248-254. Purified VLPs were separated in a 10% SDS-PAGE, and electrophoretically transferred to a nitrocellulose membrane.

Antibodies recognizing cross-reactive papillomavirus-epitopes, which are directed against denatured PV viruses are used as primary antibodies and horseraddish-peroxidase (HRP)-coupled goat-anti-rabbit/mouse-IgG served as the secondary antibody All incubations were carried out at room temperature for 1 hr, and five PBS washing steps were conducted following each incubation step. Blocking was performed with 5% bovine serum albumin (BSA). BPV1 and CPV2 L1-specific mouse antibodies were used as primary antibodies and horseraddish-peroxidase (HRP)-coupled anti-mouse IgG served as the secondary antibody (Roche Diagnostics Cooperation, Indianapolis, Ind.).

Example 9

Production of Rabbit Polyclonal Antibodies

After a prebleed, New Zealand White (NZW) rabbits were subcutaneously immunized with about 150 μg of intact TtPV L1-VLPs, or purified and concentrated dolphin-IgG plus adjuvant (TiterMax™ Gold, CytRx Corporation, Los Angeles, Calif., USA) three times at two weeks intervals. The animals were bled, the blood kept at 4° C. for 2 hrs, and blood cells separated from sera by centrifugation (400 g, 10 min). The immune response (antibody titer of the sera) was subsequently tested in Enzyme-linked Immunosorbent assay (ELISA)-studies.

Example 10

ELISA Studies

ELISA microplate (Dynatech Laboratories, Inc., Chantilly, Va.) wells were coated with: 0.1 μg TtPV VLPs or control-VLPs as intact antigen, or with up to 4 μg VLPs in denaturation buffer (1% SDS, 0.25 mM 2-mercaptoethanol, 15 mM NaCl, 20 mM Tris, pH 7.4) as disrupted antigen as described in Ghim, et al. 2004. *Biochemical and Biophysiological Research Communications* 324:1108-1115, which is incorporated herein by reference. Blocking was performed with PBS containing 5% BSA (bovine serum albumin). The coated wells were incubated with the anti-VLP antibodies of the appropriate type of TtPV. Afterwards, alkaline phosphatase (AP)-coupled goat anti-rabbit antibodies (secondary antibodies) were used. Incubation steps were performed for 1 h at 37° C., and three to five PBS-washing steps were conducted after each incubation. The adsorption was then measured at 405-410 nm (Spectra MR™, Dynex Technologies, Chantilly, Va., USA) using AP chromogenic substrate (Sigma 104 p-Nitrophenyl Phosphate; Sigma, St. Louis, Mo.).

Example 11

PV Prevalence ELISA Studies

The studies were conducted as described in Example 10, with the following changes. After coating 50 ng VLPs, animal sera were diluted 1:300 in PBS/1% BSA and incubated with the VLPs. Rabbit anti-dolphin IgG served as the first antibody, and AP-coupled goat anti-rabbit antibody was used as the secondary antibody.

Examples 1-11

Results

Isolation of TtPV-1, -2, and -3

Figure 3A:
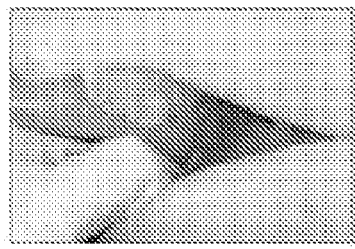
FIG. 3A is a picture showing genital condyloma of a male bottlenose dolphin living in Europe in a Portuguese aquarium, from which TtPV-1 and -3 were isolated.
Figure 3B:
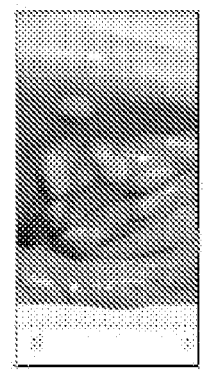
FIG. 3B is a picture showing genital lesion of a male free-ranging bottlenose dolphin (FB890) from the Charleston Harbor, S.C., USA, similar to those of lesions from a male animal (FB892) from which TtPV-2 was isolated.
Figure 4:
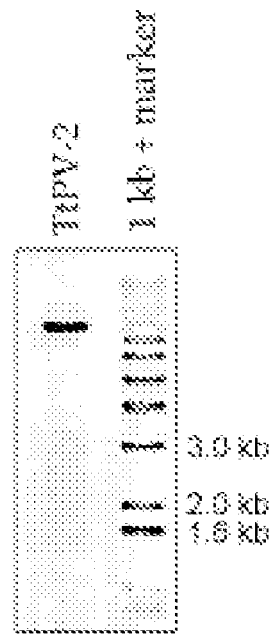
FIG. 4 is a DNA agarose gel showing the isolated, RC-amplified complete TtPV-2 sequence.
Figure 5:
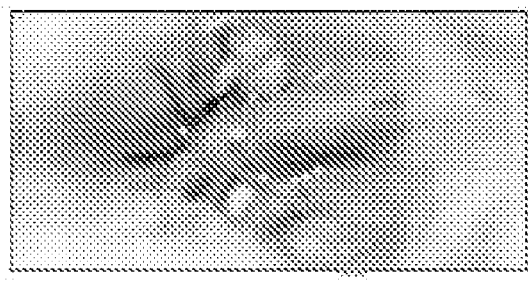
FIG. 5 is a picture showing genital lesion of a bottlenose dolphin from the Caribbean, in which TtPV-2 was demonstrated to be present using TtPV-2-specific L1-primers in conventional PCRs.

With reference to FIG. 3A, a biopsy of a genital condyloma of a captive male bottlenose dolphin from a Portuguese Aquarium was investigated for the presence of papillomaviruses. Using the isothermal, multiply primed Rolling-Circle-Amplification (RCA) technique and a subsequent digestion of the amplified products, the presence of two different DNA-fragments consistent with the typical size of a PV around 8 kb were is demonstrated, as shown in FIG. 4 (lane 1 and 2). With reference to FIG. 3B, during a dolphin health assessment study in the Charleston Harbor 08/2004 conducted by HBOI (Harbor Branch Oceanographic Institution, Inc.) and NOAA/NOS (National Oceanic and Atmospheric Administration/National Ocean Service), specimens of visually identical genital condylomas of two free-ranging animals (FB890 and FB892, FB890) were taken. With reference to FIG. 3 (lane 3), from one of those lesions (from animal FB892) a DNA-fragment of around 8 kb was isolated and amplified using. FIG. 5 shows the genital lesion of a captive dolphin from the Caribbean, which could also be shown to contain TtPV-2 (data not shown). TtPV-1 and -3 were the first isolated cetacean PVs from Europe, whereas TtPV-2 represents the first isolated North-American cetacean PV. All three types represent the first isolated PVs from bottlenose dolphins worldwide. These three viral genomes were separately cloned into pUC18 or pUC19 and fully sequenced. Genome organization of TtPVs—lack of E7 open reading frames.

Development and Detection of TtPV VLPs

The PV L1 protein represents the major component of the viral capsid. To create VLPs, the TtPV L1 nucleotide sequences are cloned into a baculovirus transfer vector downstream of the polyhedrin promoter and Sf9 insect cells are transfected with resulting recombinant baculovirus transfer vectors, respectively, and linearlized baculovirus DNA. Positive TtPV L1 recombinant baculoviruses, for each TtPV type, are plaque-purified and subsequently tested for insertion of the corresponding L1 gene using a set of primers specific flanking the polyhedrin region.

Figure 6:
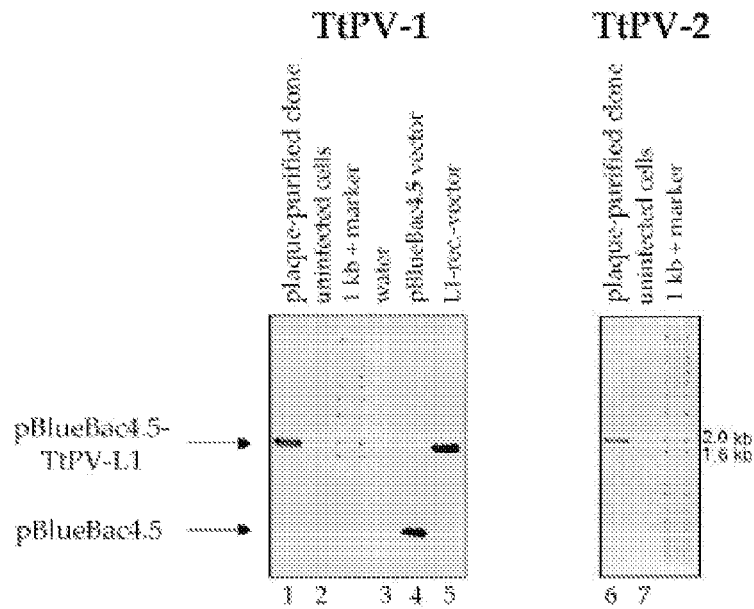
FIG. 6 displays the results of tests for the presence of the L1-genes in plaque-purified TtPV-1 L1 and TtPV-2 L1 recombinant baculoviruses in polyhedrin-specific PCRs, where lane 1 shows positive TtPV-1 L1 insect cell clones, lane 6 shows positive TtPV-2 L1 insect cell clones, lanes 2 and 7 represent uninfected insect cells as negative controls, lane 3 is water only, lane 5 is the TtPV-1 L1-recombinant pBlueBac4.5 vector used as a positive control, and lane 4 is the pBlue-Bac4.5 vector itself used as a control to determine wild-type contamination levels.

With reference to FIG. 6, lanes 1 and 6 demonstrate purified, positive recombinant TtPV-1 L1 (1524 bp) and TtPV-2 L1 (1539 bp) baculovirus clones (each product including additional 435 bp contributed by the vector). Uninfected insect cells (lanes 2 and 7) and water (lane 3) serve as negative controls, the TtPV-1 L1-recombinant pBlueBac4.5 vector (lane 5) is used as a positive control. The pBlueBac4.5 vector itself (lane 4) serves as a control to determine wild-type contamination levels. None of the plaque-purified positive TtPV-1 L1 and TtPV-2 L1 recombinant baculovirus clones (additional clones not shown) show wild-type baculovirus contamination confirming that pure, recombinant plaques were obtained.

In immunofluorescence assays on Sf9 cells infected with recombinant baculovirus maintaining TtPV-1 with known, broadly cross-reactive monoclonal antibodies (AU-1, AU-5, and AU-6) which are generated against disrupted BPV-1 (Bovine Papillomavirus type 1). See Nakai, et al. 1986. *Intervirology* 25:30-37 and Jenson, et al. 1997 *Immunologic research* 16:115-119, which are incorporated herein by reference. No cross-reactivity was detected (data not shown), although Sf9 cells were inoculated with high titer recombinant baculovirus expressing L1, indicating that TtPV-1 L1 does not carry broadly cross-reactive epitopes recognized by these well-known monoclonal antibodies and the difference of TtPV-1 L1 to other known L1 proteins. Immunofluorescence assays carried out with polyclonal, specifically generated rabbit anti-TtPV-VLPs confirmed L1 expression and VLP assembly in the insect cells.

To determine cross-reactivity of known antibodies against PV L1 proteins with both dolphin PV L1 proteins in a western blot, purified TtPV-1 and -2 VLPs were separated in 10% sodium dodecyl sulfate polyacrylamide gels (SDS-PAGE) and transferred to a nitrocellulose membrane.

Figure 7:
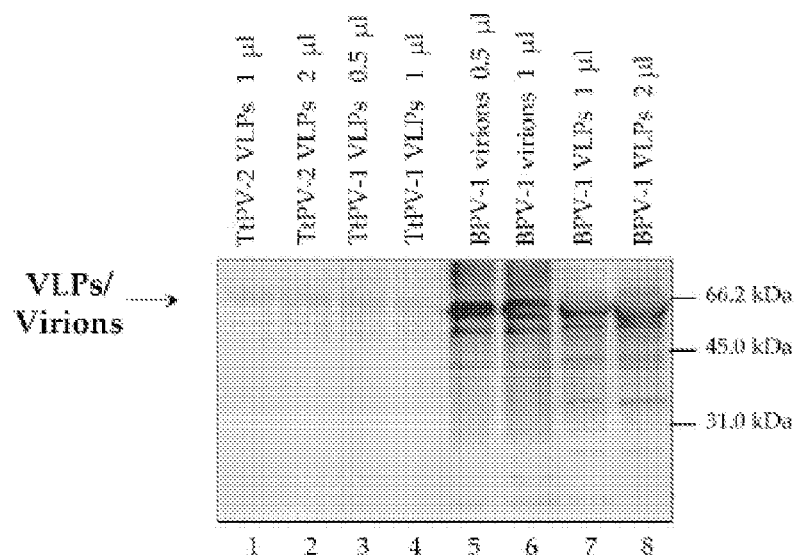
FIG. 7 is a Western blot where purified VLPs from TtPV-1 L1-recombinant infected Sf9 insect cells in lanes 3 and 4, where VLPs from TtPV-2 L1-recombinant infected Sf9 insect cells in lanes 1 and 2, and where BPV-1 virions (lanes 5 and 6) and BPV-1 VLPs (lanes 7 and 8) serve as positive controls.

With reference to FIG. 7, polyclonal antibodies raised against denatured antigens of BPV-1 L1, VLPs of TtPV-1 (lanes 3 and 4) as well as of TtPV-2 (lanes 1 and 2) were identified as being composed of PV L1 protein. Both TtPV-1 and TtPV-2 purified VLPs carry weakly cross-reactive epitopes recognized by this polyclonal antibody. BPV-1 virions (lanes 5 and 6) and BPV-1 VLPs (lanes 7 and 8) serve as positive controls.

With reference to FIGS. 2 and 8A-9B, transmission electron microscopy pictures demonstrated the structural quality of the generated VLPs, which were self-assembled into particles of a structure and size expected for a papillomaviruses Icosahedral capsomers are identified. Additionally, the VLPs self-assemble into particles of the expected PV-typical size of around 55 nm. The presence of single capsomers in high concentrations was also noticed.

Neutralizing Antibodies Against TtPV VLPs Only Target Intact Particles

With reference to FIG. 10, by injecting purified and concentrated IgG from combined serum of two different free-ranging dolphins, which do not display any sign of a disease or infection into rabbits, polyclonal α-dolphin-IgG antibodies are generated as antibodies to be used in ELISA assays, western blots, and immunofluorescence studies.

With reference to FIG. 11, the polyclonal rabbit-anti-TtPV-1 and -TtPV-2 VLPs are generated, purified, and used in ELISA studies to determine whether they target conformational and/or linear epitopes of the corresponding VLPs. ELISA plates were coated with: (A) intact purified TtPV-1 VLPs, (B) denatured TtPV-1 VLPs, (C) intact purified TtPV-2 VLPs, or (D) denatured TtPV-2 VLPs, respectively. The following served as primary antibodies: (E) sera from rabbits immunized with TtPV-1 VLPs, (F) sera from rabbits immunized with TtPV-1 VLPs, (G) sera from rabbits immunized with TtPV-2 VLPs, and (F) sera from rabbits immunized with TtPV-2 VLPs. Alkaline phosphatase-coupled goat-anti-rabbit antibodies were used as secondary antibodies. Different dilutions of the antibodies from rabbit 1 give a strong signal with 100 ng intact type 1 VLPs (A/F). The value nearly does not change using dilutions from 1:100 to 1:1,000. The same antibodies weakly cross-reacted with type 2 particles (C/F). Different dilutions of the antibodies from rabbit 2 give good signals with type 2 VLPs, but weaker (C/H). An even higher reaction of the same antibodies with type 1 VLPs is observed (A/H). No reaction, neither with the sera (E, G), nor with denatured VLPs in 40-fold excess (B, D), in comparison to used intact particles, could be detected, suggesting the antibodies against the VLPs only target correctly assembled particles and are neutralizing.

PV Prevalence in Atlantic Bottlenose Dolphin Populations.

TtPV L1-VLPs were used in seroepidemiological studies to screen dolphin populations for PV infection. Results suggest the PV prevalence in free-ranging and captive bottlenose dolphins is high.

Four dolphin populations representing 115 animals were investigated. Eighty of these dolphins are free-ranging animals inhabiting the estuarine waters of Charleston, S.C. (CHS) and the Indian River Lagoon, Fla. (IRL) assessed for health during annual Atlantic bottlenose dolphin health assessment studies. The other two populations represent 35 captive animals held in two different facilities. Within this CHS group, a dolphin which had displayed the genital lesion from which TtPV2 was isolated served as a positive control. See Rehtanz, et al. 2006. Journal of General Virology 87:3559-3565, which is incorporated herein by reference.

About 82-100% of the sera samples from free-ranging Atlantic bottlenose dolphins positively reacted with coated TtPV VLPs. About 59% of the dolphins held in the US-facility carried anti-PV antibodies, while 38% of the sera obtained from dolphins maintained in the European facility showed reactivity. Positive ELISA values were not linked to gender. Age when attaining sexual maturity is variable among bottlenose dolphins. On average, females become sexually mature when they reach about 2.3 m in length, at approximately five to twelve years, while males become sexually mature when they reach about 2.4 to 2.6 m, at approximately ten to twelve years. Although ELISA levels generally did not seem to be associated with age, premature animals tended to be negative.

Throughout this document, various references are mentioned. All such references are incorporated herein by reference, including the references set forth in the following list:

Anttila, T., P. Saikku, P. Koskela, A. Bloigu, J. Dillner, I. Ikaheimo, E. Jellum, M. Lehtinen, P. Lenner, T. Hakulinen, A. Narvanen, E. Pukkala, S. Thoresen, L. Youngman, J. Paavonen. 2001. Serotypes of Chlamydia Trachomatis and Risk for Development of Cervical Squamous Cell Carcinoma. JAMA. 285(1):47-51.

Barr, B., J. L. Dunn, M. D. Daniel, A. Banford. 1989. Herpes-like viral dermatitis in a beluga whale (*Delphinapterus leucas*). J. Wildl. Dis. 25:608-611.

Bossart, G. D., C. Cray, J. L. Solorzano, S. J. Decker, L. H. Cornell and N. H. Altman. 1996. Cutaneous papovaviral-like papillomatosis in a killer whale (Orcinus orca). Mar. Mamm. Sci. 12:274-281.

Bossart, G. D., R. Ewing, M. Sweat, S. Decker, C. Walsh, S.-J. Ghim and A. B. Jenson. 2002. Viral papillomatosis in Florida manatees (*Trichechus manatus latirostris*). Exp. Mol. Pathol. 72:37-48.

Bossart, G. D., Ghim, S.-J., Rehtanz, M., Goldstein, J., Varela, R., Ewing, R., Fair, P. A. Lenzi, R., Joseph, B., Hicks, C., Schneider, L., McKinnie, C. J., Reif, J. S., Sanchez, R., Lopez, A., Novoa, S., Bernal, J., Goretti, M., Rodriguez, M., Defran, R. H., and Jenson, A. B. 2005. Orogenital neoplasia in Atlantic bottlenose dolphins (*Tursiops truncates*). Aquatic Mammals 31(4):473-480.

Cassonnet, P., M. F. Van Bressem, C. Desaintes, K. Van Waerebeek, G. Orth. 1998. Abstract. Papillomaviruses cause genital warts in small cetaceans from Peru. The World Marine Mammal Science Conference, Monaco, January 1998.

Chow, L., and T. Broker. 1994. Papillomavirus DNA replication. Intervirology. 37:150-158.

Ghim, S.-J., A. Rector, H. Delius, J. P. Sundberg, A. B. Jenson, M van Ranst. 2004. Equine papillomavirus type 1: complete nucleotide sequence and characterization of recombinant virus-like particles composed of the EcPV-1 L1 major capsid protein. Bioch. Biophys. Res. Commun. 324(3):1108-1115.

Holt, S., G. Schuller, and V. Wilson. 1994. DNA binding specificity of the bovine papillomavirus E1 protein is determined by sequences containing within an 18 base-pair inverted repeat element at the origin of replication. J. Virol. 68: 1094-1102.

Hou, S. Y., S. Y. Wu, and C. M. Chiang. 2002. Transcriptional Activity among High and Low Risk Human Papillomavirus E2 Proteins Correlates with E2 DNA Binding. J. Biol. Chem. 277:45619-45629.

Howley, P. M., and D. R. Lowy. 2001. Papillomaviruses and Their Replication. Fields Virology. 4th edition; Raven Press, Philadelphia: 2197-2229.

Jenson, A. B., M. C. Jenson, L. Cowsert, S.-J. Ghim, and J. P. Sundberg. 1997. Multiplicity of Uses of Monoclonal Antibodies That Define Papillomavirus Linear Immunodominant Epitopes. Immunol. Res. 16:115-119.

Kennedy, S., I. J. Lindstedt, M. M. Mc Aliskey, S. A. McConnell, S. J. McCullough. 1992. Herpesviral encephalitis in a harbor porpoise (*Phocoena phocoena*). J. Zoo Wildl. Med. 23:374-379.

Lambertsen, R. H., B. A. Kohn, J. P. Sundberg, C. D. Buergelt. 1987. Genital papillomatosis in sperm whale bulls. J. Zoo Wildl. Med. 23:374-379.

Martina, B. E. E., T. C. Harder, and A. D. M. E. Osterhaus. 2003. Genetic characterization of the unique short segment of Phocid herpesvirus type 1 reveals close relationships among alphaherpesviruses of hosts of the order Carnivora. J. Gen. Virol. 84:1427-1430.

Martineau, D., A. Lagace, P. Beland, R. Higgins, D. Armstrong, L. R. Shugart. 1988. Pathology of stranded beluga whales (*Delphinapterus leucas*) from the St. Lawrence Estuary, Quebec, Canada. J. Comp. Pathol. 98:287-311.

Morris, R. J., Lockyer C. 1988. Twenty-two months in the life of a juvenile wild bottlenose dolphin. Aquat. Mamm. 14:49-62.

Nakai, Y., W. D. Lancaster, L. Y. Lim, and A. B. Jenson. 1986. Monoclonal Antibodies to Genus- and Type-Specific Papillomavirus Structural Antigens. Intervirology. 25:30-37.

Norris, K. S., and T. P. Dohl. 1980. The structure and function of cetacean schools. Herman L M (ed). Cetacean behavior: mechanisms and functions, John Wiley & Sons, New York, p. 267-291.

Rector, A., G. D. Bossart, S.-J. Ghim, J. P. Sundberg, A. B. Jenson, and M. van Ranst. 2004. Characterization of a Novel Close-to-Root Papillomavirus from a Florida Manatee by Using Multiply Primed Rolling-Circle Amplification: *Trichechus manatus latirostris* Papillomavirus Type 1. J. Virol. 78:12698-12702.

Sedman, J., and A. Stenlund. 1995. Co-operative interaction between the initiator E1 and the transcriptional activator E2 is required for replicator specific DNA replication of bovine papillomavirus in vivo and in vitro. EMBO J. 14: 6218-6228.

Van Bressem, M. F., K. Van Waerebeek, A. Garcia-Godos, D. Dekegel, P. P. Pastoret. 1994. Herpes-like virus in dusky dolphins Lagenorhynchus obscurus, from coastal Peru. Mar. Mamm. Sci. 10:354-359.

Van Bressem, M. F., K. Van Waerebeek, G. Piérard, C. Desaintes. 1996. Genital and lingual warts in small cetaceans from coastal Peru. Dis. Aquat. Org. 26:1-10.

Van Bressem, M. F. 1997. Natural history of virus infections in cetaceans. PhD thesis, University of Liege.

Van Bressem, M. F., R. A. Kastelein, P. Flamant, G. Orth. 1999a. Cutaneous papillomavirus infection in harbour porpoise (*Phocoena phocoena*) from the North Sea. Vet. Rec. 144:592-593.

Van Bressem, M. F., K. Van Waerebeek, J. A. Raga. 1999b. A review of virus infections of cetaceans and the potential impact of morbilliviruses, poxviruses and papillomaviruses on host population dynamics. Dis. Aquat. Org. 38:53-65.

Jenson, A. B., J. D. Rosenthal, C. Olson, F. Pass, W. D. Lancaster, and K. Shah. 1980. Immunologic relatedness of papillomaviruses from different species. Journal of the National Cancer Institute 64:495-500.

Mead, J. G., and C. W. Potter. 1990. Natural history of bottlenose dolphins along the central Atlantic coast of the United States. Academic Press, San Diego, Calif.

Odell, D. K. 1975. Status of aspects of the life history of the bottlenose dolphin, *Tursiops truncatus*, in Florida. Journal of Fishery Research Board of Canada 32:1055-1058.

Rehtanz, M., S.-J. Ghim, A. Rector, M. Van Ranst, P. A. Fair, G. D. Bossart, and A. B. Jenson. 2006. Isolation and characterization of the first American bottlenose dolphin papillomavirus: *Tursiops truncatus* papillomavirus type 2. Journal of General Virology 87:3559-3565.

U.S. Pat. No. 5,057,411 to Lancaster et al., issued Oct. 15, 1991, entitled "Type-specific papillomavirus DNA sequences and peptides,"

U.S. Pat. No. 5,874,089 to Schlegel et al., issued Feb. 23, 1999, entitled "Protecting against canine oral papillomavirus (COPV),"

U.S. Pat. No. 6,485,728 to Schlegel et al., issued Nov. 26, 2002, entitled "Formalin-Inactivated human papillomavirus L1 protein vaccine,"

U.S. Pat. No. 6,887,478 to Schlegel et al., issued May 3, 2005, entitled "Formalin-treated human papillomavirus L1 protein vaccine,"

United States Patent Application Publication No. 2002/0197264 of Schlegel, et al., published Dec. 26, 2002, entitled "Protecting against canine oral papillomavirus (COPV),"

United States Patent Application Publication No. 2004/0086527 of Schlegel, et al., published May 6, 2004, entitled "Protecting against canine oral papillomavirus (COPV),"

Yuan H, Ghim S, Newsome J, Apolinaro T, Olcese V, Martin M, Delius H, Felsburg P, Jenson B, Schlegel R. An epidermotropic canine papillomavirus with malignant potential contains an E5 gene and establishes a unique genus. *Virology* 2006; Oct. 9, 2006 electronic publication.

Ghim, S, Basu, P S, and Jenson, A B. Cervical cancer, etiology, pathogenesis treatment and future vaccines. Asian Pacific Journal of *Cancer Prevention* 3 (3), 207-214, 2002.

Ghim S., J. A. Suzich, J. Tamura, J. A. Bell, W. White, J. Newsome, F. Hill, P. Warrener, J. Sundberg, A. B. Jenson and R. Schlegel. Formalin-inactivated oral papilloma extracts and recombinant L1 vaccines protect completely against mucosal papillomavirus infection: a canine model. *Vaccines* 95, 375-379, 1995.

Pastrana D V, Gambhira R, Buck C B, Pang Y Y, Thompson C D, Culp T D, Christensen N D, Lowy D R, Schiller J T, Roden R B. Cross-neutralization of cutaneous and mucosal Papillomavirus types with anti-sera to the amino terminus of L2. *Virology*. 337:365-72, 2005.

U.S. Pat. No. 7,001,995 to Neeper et al., issued Feb. 21, 2006, entitled "Synthetic human papillomavirus genes,"

U.S. Pat. No. 6,908,615 to Hofmann et al., issued Jun. 21, 2005, entitled "DNA encoding human papilloma virus type 18,"

United States Patent Application Publication No. 2005/0026257 of Gissmann, et al., published Feb. 3, 2005, entitled "Production and applications for polyvalent vaccines against diseases caused by papilloma viruses,"

U.S. Pat. No. 6,165,471 to Garcea et al., issued Dec. 26, 2000, entitled "Homogeneous human papillomavirus capsomere containing compositions, methods for manufacture, and use thereof as diagnostic, prophylactic or therapeutic agents,"

U.S. Pat. No. 6,153,201 to Rose et al., issued Nov. 28, 2000, entitled "Oral immunization with papillomavirus virus-like particles,"

U.S. Pat. No. 5,643,765 to Willey, issued Jul. 1, 1997, entitled "Method for quantitative measurement of gene expression using multiplex competitive reverse transcriptase-polymerase chain reaction,"

U.S. Pat. No. 5,639,606 to Willey, issued Jun. 17, 1997, entitled "Method for quantitative measurement of gene expression using multiplex competitive reverse transcriptase-polymerase chain reaction,"

U.S. Pat. No. 5,283,171 to Manos et al., issued Feb. 1, 1994, entitled "Compositions for and detection of human papillomavirus by specific oligonucleotide polymerase primers using the polymerase chain reaction,"

United States Patent Application Publication No. 2006/0029612 of Palmer, et al., published Feb. 9, 2006, entitled "Prevention and treatment of recurrent respiratory papillomatosis,"

United States Patent Application Publication No. 2005/0282263 of McCormick, et al., published Dec. 22, 2005, entitled "Flexible vaccine assembly and vaccine delivery platform."

What is claimed is:

1. A immunogenic composition for conferring protection against *Tursiops truncatus* papillomavirus (TtPV) infection in a subject susceptible to TtPV infection, comprising a virus-like particle assembled from a TtPV L1 protein, wherein said TtPV is selected from the group consisting of TtPV-1 and TtPV-2.

2. The immunogenic composition of claim 1, wherein said TtPV is TtPV-2.

3. The immunogenic composition of claim 1, wherein said TtPV is TtPV-1.

4. The immunogenic composition of claim 1, wherein the vaccine comprises virus-like particles assembled from at least two TtPV L1 proteins, wherein said at least two TtPVs are TtPV-1 and TtPV-2.

5. The immunogenic composition of claim 1, and further comprising an adjuvant.

6. A method of protecting a subject against TtPV infection by administering the immunogenic composition of claim 1.

7. The method of claim 6, wherein said TtPV is TtPV-2.

8. The method of claim 6, wherein said TtPV is TtPV-1.

9. The method of claim 6, wherein said administered vaccine comprises virus-like particles assembled from at least two TtPV L1 proteins, wherein said at least two TtPVs are TtPV-1 and TtPV-2.

10. A method of diagnosing TtPV infection in a subject, comprising:
  providing a virus-like particle assembled from at least one TtPV L1 protein, selected from the group consisting of TtPV-1 and TtPV-2;
  contacting the virus-like particle with serum obtained from the subject; and
  identifying the subject as having TtPV infection if a TtPV antibody capable of binding the virus-like particle is detected in the serum.

11. The method of claim 10, wherein the binding is detected using an antibody capable of binding the TtPV antibody.

* * * * *